(12) United States Patent
Halamish et al.

(10) Patent No.: US 7,757,352 B2
(45) Date of Patent: Jul. 20, 2010

(54) STERILE HANDLE COVERS

(76) Inventors: Asaf Halamish, 10 Shaananim St., Pardes Hanna (IL) 37063; Joseph Shachar, 12 Shmuel Hanagid St, Ramat Hasharon (IL) 47295; Benjamin Spenser, 22 Zamir St., Caesarea (IL) 38900; Dror Mizra, 28 Duvnov St., Holon (IL) 58809

( * ) Notice: Subject to any disclaimer, the term of this patent is extended or adjusted under 35 U.S.C. 154(b) by 987 days.

(21) Appl. No.: 10/598,076

(22) PCT Filed: Feb. 20, 2005

(86) PCT No.: PCT/IL2005/000207

§ 371 (c)(1), (2), (4) Date: Aug. 17, 2006

(87) PCT Pub. No.: WO2005/079156

PCT Pub. Date: Sep. 1, 2005

(65) Prior Publication Data
US 2009/0133226 A1 May 28, 2009

(30) Foreign Application Priority Data
Feb. 19, 2004 (IL) ........................... 160468

(51) Int. Cl.
*B25G 1/10* (2006.01)
(52) U.S. Cl. .......................... 16/421; 16/906; 362/400

(58) Field of Classification Search .................. 16/421, 16/422, 110.1, 906, DIG. 12, DIG. 24; 74/551.8, 74/551.9, 558.5; 150/155; 362/399, 400, 362/804; 206/223, 438
See application file for complete search history.

(56) References Cited

U.S. PATENT DOCUMENTS

| | | | | | |
|---|---|---|---|---|---|
| 4,559,671 | A | * | 12/1985 | Andrews et al. | 16/421 |
| 4,605,124 | A | * | 8/1986 | Sandel et al. | 206/223 |
| 4,976,299 | A | * | 12/1990 | Bickelman | 150/155 |
| 5,036,446 | A | * | 7/1991 | Quintanilla et al. | 362/399 |
| 5,156,456 | A | * | 10/1992 | Hoftman et al. | 362/400 |
| 5,465,461 | A | * | 11/1995 | Sandel | 16/421 |
| 5,469,600 | A | * | 11/1995 | Sandel | 16/421 |
| 5,669,102 | A | * | 9/1997 | Sandel | 16/421 |
| 5,709,465 | A | * | 1/1998 | Lanzone | 362/400 |
| 5,735,598 | A | * | 4/1998 | Ramirez | 362/400 |
| 5,884,996 | A | * | 3/1999 | Cottone et al. | 362/399 |
| 6,447,149 | B1 | * | 9/2002 | Kaforey et al. | 362/400 |
| 6,692,141 | B2 | * | 2/2004 | Jesurun et al. | 362/399 |

* cited by examiner

*Primary Examiner*—William L. Miller

(57) ABSTRACT

A disposable sterile handle cover uses a flexible bag, a portion of the open side of which is held snugly by a retaining ring to the inside of a conical skirt. A first set of spikes include variable length spikes protruding from the inner wall, to secure the bag against the handle. A second set of spikes protrude inwardly from the retaining ring and promote stretching and orderly application of the to the handle.

2 Claims, 3 Drawing Sheets

STERILE HANDLE COVERS

FIELD OF THE INVENTION

The present invention relates to disposable sterile handle covers. A particular application is a disposable sterile handle cover for lighting bodies in operating rooms.

BACKGROUND OF THE INVENTION

Medical appliances, particularly operating room equipment, must be kept sterile. Many surgical instruments are taken away from the operating room between operations to be cleaned and sterilized. However large or sensitive instruments, equipment and operating room fixtures cannot be easily moved. For example, devices such as surgical lamps cannot be removed from the operating room between operations. Such appliances are therefore cleaned and sterilized in situ. The handles of the lamps are of special concern because they are frequently handled during operations. Such lamp handles typically have associated cylindrical projections with a conical base connecting it to the lamp assembly. The conical base provides insulation from the heat generated by the lamp, a resting point for the hand for increased leverage when adjusting the position of the lamp and a barrier to prevent the hand from sliding beyond the handle exposing un sterilized parts.

In the past, surgical lamps have been sterilized between operations by spraying an antiseptic solution. This procedure however is far from sufficient. Nowadays the use of reusable detachable handles is commonplace. Such handles can be sterilized in an autoclave before each surgical procedure. The disadvantages of such a practice are the operational inconvenience of dismantling, sterilizing and reassembly and the considerably high rate of wearing out of the handles, which are typically made of plastics, as a result of the high temperatures involved.

U.S. Pat. No. 4,605,124 discloses disposable covers for handles of lighting fixtures made of a flexible plastic, latex or rubber. The covers are molded to closely conform with the shape of a handle. An adaptation kit consisting of a substitute handle and attaching means to the lamp assembly is provided in such cases in which the dimensions of the original handle do permit fitting of the disposable cover. The disposable cover consists of a grip and a flange. The flange is flat, or conically shaped fitted to cover the handle base. The cover is attached to the handle either by means of the flange, its rim, or detent means and or snap ring attaching the cover to the grip of the handle. The flange rim is preferably slightly undersized relative to the handle base providing a snap over fit. An improved attachment of the cover is achieved by adhering the flange to the handle base. The main disadvantage of using such covers is that often, there is a need to replace the original lamp handle. The substituting handle is made to fit the disposable handle cover. This process is expensive and necessitates replacement of a well-designed handle by a lesser grade design. Another difficulty associated with such covers is that they are typically held in place with adhesives. Therefore it must be replaced after repeated use due to a buildup of adhesive residue.

U.S. Pat. No. 4,976,299 discloses a sterile disposable plastic cover for a handle of an operating room lighting fixture. The cover includes a hollow member closed at one end and open at its other end. Around the open end is attached a hand guard. The open end is partially restricted with a retention member permitting the handle of the lighting fixture to extend through the open end of the hollow member and holding it in place. The retention member is preferably a disc having intersecting slits, which define an opening smaller than the handle and the opened end of the hollow member. The cover is attached to the handle by friction exerted by the retention member being pressed against the surface of the handle. This solution has its drawbacks for example, in order to accommodate the large variety of dimensions of handles available, there is a need for several different sterile disposable plastic covers having different lengths and bore sizes. Although the retention elements formed intersecting slits of the retention member are flexible and therefore can accommodate a range of handle sizes, the component of the force which is normal to the handle surface decreases as the stripes are more extremely bent. Therefore several different bore radii and corresponding lengths of the intersecting slits are required to provide a firm attachment of a disposable cover to a variety of available handles. Furthermore the hollow member has to be secured to the light handle lest it should fall off. Employing a cover having a too long hollow member might interfere with the operation of the operating team while adjusting the light fixture during the procedure. All these factors are considered when buying or maintaining the appliances in a hospital.

DETAILED DESCRIPTION OF THE PRESENT INVENTION

According to one embodiment of the invention there is provided a disposable sterile handle cover (DSHC), highly adaptable in terms of size, for application onto actuating handles of equipment or fixtures. The DSHC of the invention consists of a substantially tubular bag open at one end, hereinafter referred to as flexible handle cover bag (FHCB). At its open end, a portion of the FHCB is gripped around its entire periphery by a collar as will be described below with reference to FIGS. 1-6.

Figure 1:
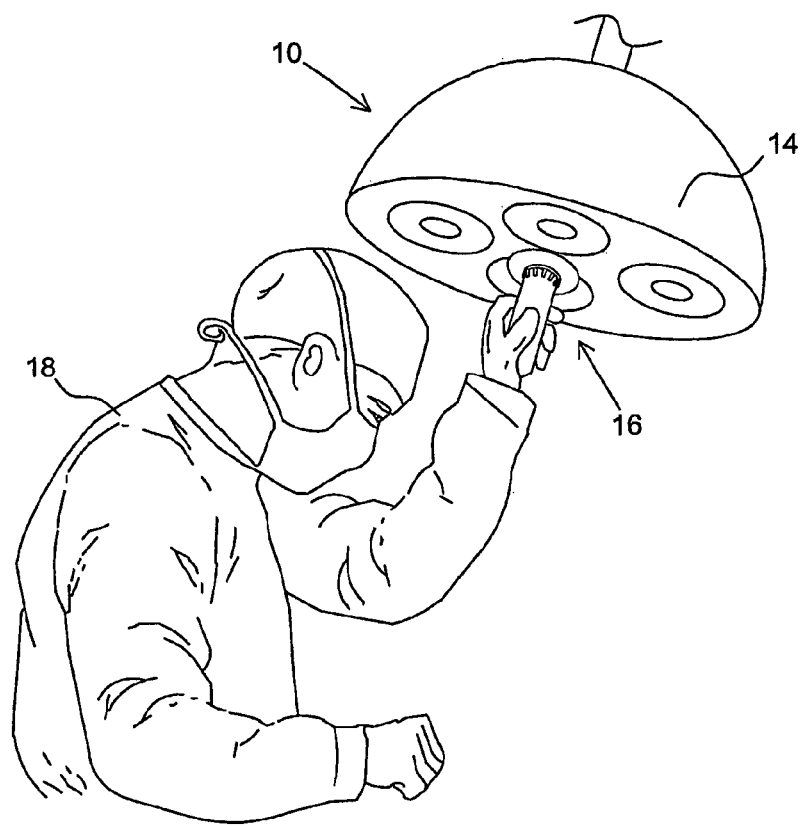
FIG. 1 is an isometric view of a surgical lighting fixture system in use with a disposable sterile handle cover in accordance with the present invention.
Figure 2:
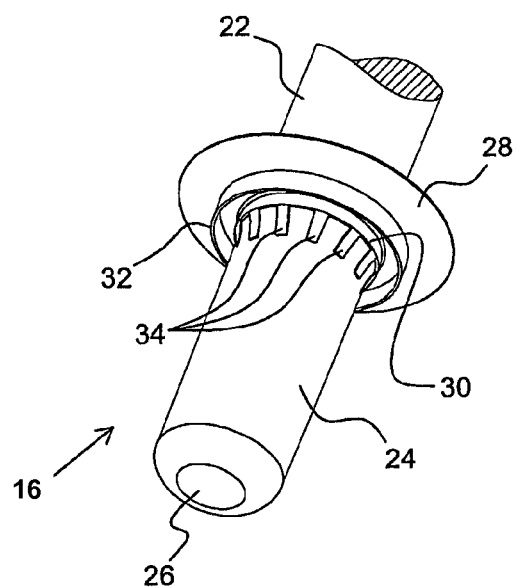
FIG. 2 is an isometric view of the disposable sterile handle cover of FIG. 1 being installed on a handle of a light fixture.

In FIG. 1 the use of a DSHC of the invention is schematically shown. A surgical lighting fixture 10 has a body 14 and a manual handle covered by a DSHC 16, manipulated by a member of the surgical team 18. In FIG. 2 an isometric view of the DSHC according to a preferred embodiment of the invention is shown stretched on a handle of a surgical light fixture. A DSHC, such as DSHC 16 is applied on handle 22 of a light fixture. A flexible handle cover bag (FHCB) 24 covers the lower section of handle 26 is at the bottom. The open end of the FHCB 24 is attached to a skirt 28 by means of an inner ring 30 which together make up the collar. Ring 32 integrally connected to the skirt 28 increases its structural strength. A set of spikes 34 protruding from the inner ring 30 maintain the FHCB 24 stretched as the DSHC is slid upwards as it is applied over handle 22.

Figure 3:
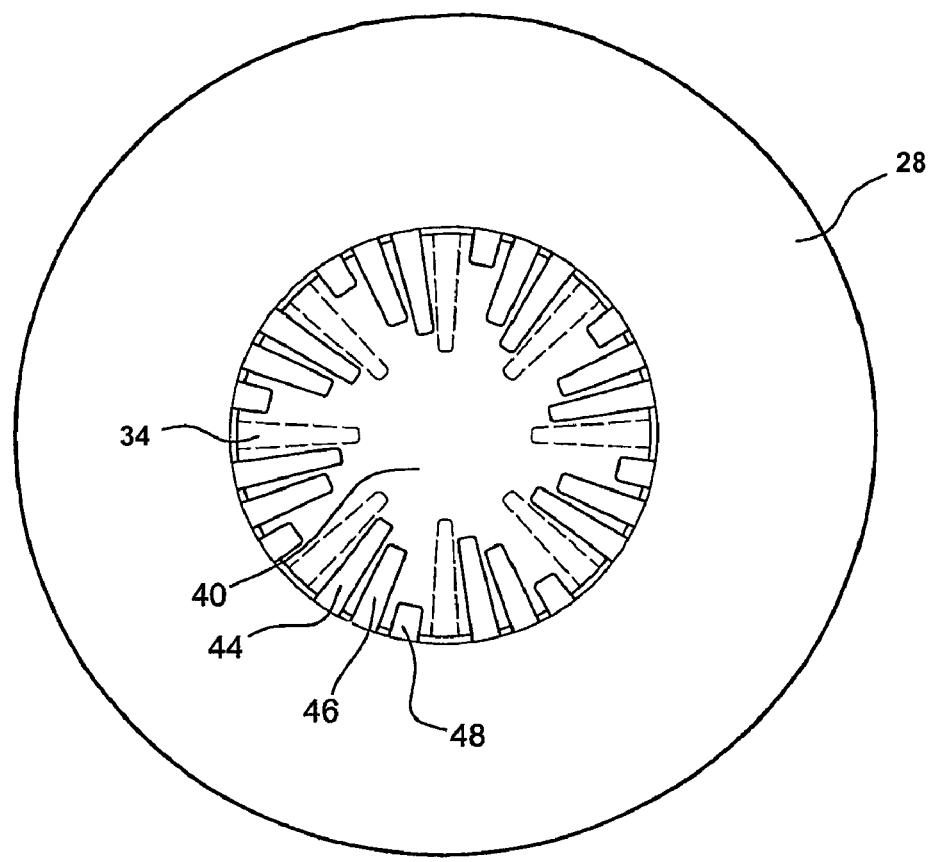
FIG. 3 is a topside view of the disposable sterile handle cover of FIG. 1.
Figure 4:
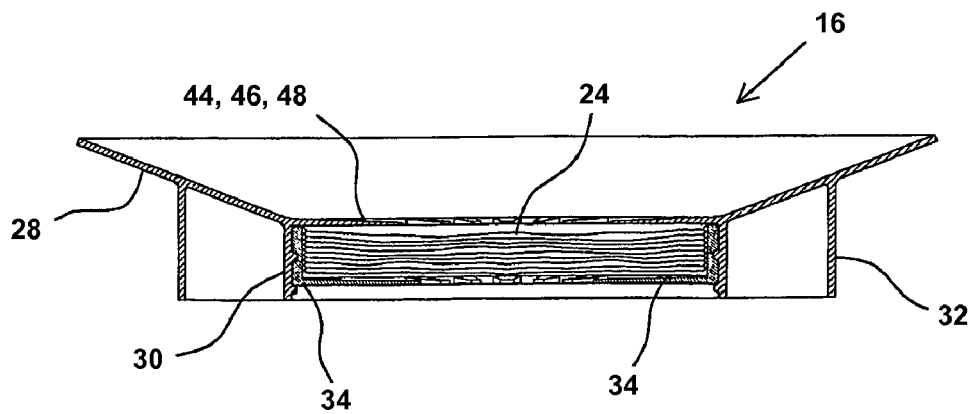
FIG. 4 is a longitudinal sectional view of a skirt of the disposable sterile handle cover, prior to installation on the light fixture.
Figure 5:
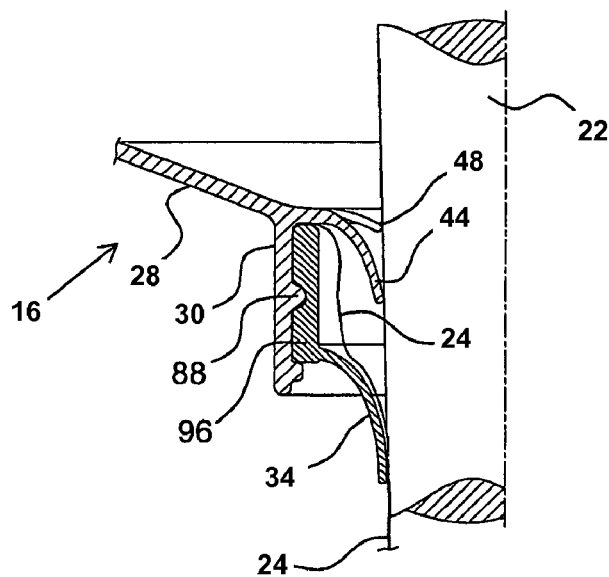
FIG. 5 is a partial view of a longitudinal section of the disposable sterile handle cover, after installation on the light fixture.
Figure 6:
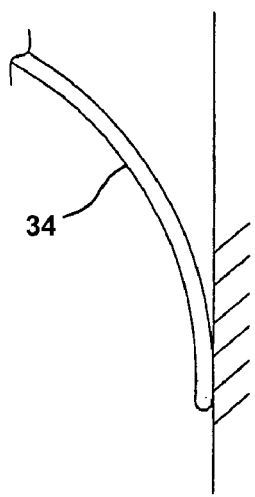
FIG. 6A is a schematic presentation of the components of the force exerted by an extremely bent spike of the installation on the light fixture.
FIG. 6B is a schematic presentation of the components of the force exerted by a slightly bent spike of the installation on the light fixture.
Figure 6:
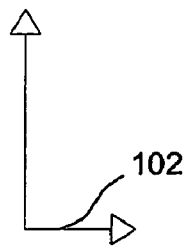
Figure 6:
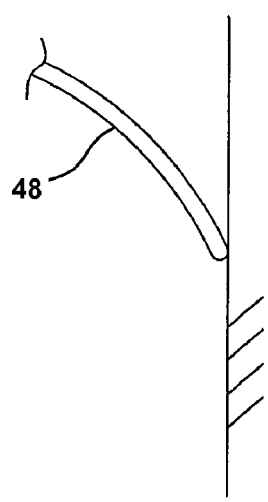
Figure 6:
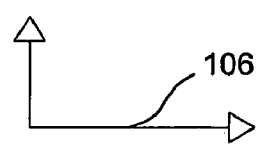

In FIG. 3 a topside view of the DSHC 16. Central aperture 40 at the annular skirt 28 permits sliding of the DSCH over a handle of a light fixture. The aperture 40 forms a continuum with the lumen of the FHCB (not shown). A set of spikes including such as spikes 44, 46 and 48 having different lengths protrude from the skirt inwards, towards its center. The handle when pushed into the aperture 40 bends some or all of these spikes, depending on their respective lengths. Spike 44 is longer than spike 46 and 48. Spikes 34, disposed at a different level than spikes 44, 46 and 48, as seen in FIGS. 3-5, support the FHCB maintaining it stretched during its installation as described above. Variants of the embodiment of the invention have more than one layer of spikes and/or more than three different spikes protruding from the skirt. Typically the inner diameter of a DSHC of the invention accommodates a range of handles widths as known in the market, taking into consideration that small width diameters are to at least reach the longest spikes and bend them. Such a DSHC is suitable for handles of light fixtures having widths in a range that at least bends spikes such as spike 44, and no more than the width required to bend spikes 48. The length of an FHCB of the Invention is made to accommodate the maximal length of available handles.

In FIG. 4 a section along the longitudinal axis of a DSHC, in a pre-application state is shown. DHSC 16 has a conical skirt 28 integral with ring or strengthening cylinder 32 and an inner ring or cylinder 30 coaxial with the skirt. The entire FHCB 24 is folded to fill in the space between spikes 34 and spikes such as spikes 44, 46, and 48. In this state the DHSC is compact which is useful for handling, saves place in storage and occupies a small storage space and a saves on the small sterile packaging. The two sets of spikes, namely the set below the folded FHCB 24 and above the FHCB 24 help secure the FHCB folded.

In FIG. 5 a longitudinal sectional view of a DSHC 16 is shown applied over handle 22. Skirt 28 has an inner cylinder 30 having one or more peripheral Ridges. Ridge 88 is substantially located at the middle of the inner surface of the cylinder wall 30. A longer spike 44 and a shorter spike 48 protrude from the inner rim of the skirt 28 inwards, towards the longitudinal axis of the skirt, bending downwards by the force applied by handle 22. An inner ring 96, which is a retention ring snugly fits into cylinder 30. The mutual hold is strengthened by means of ridge 88 that fits in a compatible groove in inner ring 96. A set of spikes 34 protrude from the retention ring 96 towards the center of the skirt, these spikes are referred to hereinafter as Inner ring spikes (IRSs). The tubular FHCB 24 is held tightly between ring 96 and the cylinder 30 of skirt 28, curving downwards such that the IRSs 34 keep it tightly set against handle 22, which promotes orderly application of FHCB 24 on the handle.

In FIGS. 6A and 6B the forces exerted by the spikes of the DSHC on the handle are schematically illustrated. The force exerted by a long and extremely bent spike is presented in FIG. 6A. The bent spike 34 exerts a normal component 102 of the bending force on handle, being proportional to the friction force generated between the spike and the handle. In FIG. 6B a shorter spike for example, shorter spikes 48 is considerably less curved than the longer spike 34 and exerts a significantly higher normal component of force 106 inducing a significantly higher friction force. Therefore the combination of multiple lengths of spikes promotes adaptation of the DSHC of the invention to various handle widths. The distribution of spike lengths ensures that for every handle width available, at least some spikes will generate a stronger friction force above such a threshold as to hold the DSHC secured to the handle. The additional layer of IRSs serves mainly for stretching the FHSC along the grip of the handle from its bottom up, but also supports securing the DSHC to the handle of the operating room appliance.

A DSHC according to the invention is preferably made of an elastomer such as plastic materials, or latex or synthetic rubber, of kinds typically used for manufacturing medical disposable accessories. The skirt and the Inner ring of a DSHC are made relatively thick. The required manufacturing tolerances are substantially wide which potentially reduce the cost of manufacturing. FHCB is made considerably thin with respect to the skirt, typically employing blow moulding techniques. Therefore the cost of manufacturing can be kept substantially low.

The skirt of the DSHC fits in any case, in which the handle base is practically absent, flat, conically, or bell shaped. It is attached to the handle by means of the friction exerted between its spikes and the handle. The skirt provides a resting point for the hand for an increased leverage when adjusting the position of the lamp and a barrier preventing the hand from sliding beyond the handle. It also provides thermal Insulation from heat generated by the lighting fixture.

The invention claimed is:

1. A cover for a handle for use under sterile conditions, the cover comprising:
    a flexible, foldable bag open at one end, to cover said handle;
    an annular skirt for holding the open end of said flexible bag;
    a ring for snugly holding said bag against the inner surface of said skirt;
    a first set of spikes of differing lengths protruding inwards from the inner surface of said skirt, pointing towards a longitudinal axis of said skirt; and
    a second set of spikes protruding inwards from an inner perimeter of said ring.

2. A method for providing a sterile cover to a handle in an operating room comprising:
    unfolding a folded sterile bag, with its open end directed towards said handle, starting said unfolding from the end of said handle by sliding a collar secured to the open end of the bag along said handle, the collar comprising an annular skirt and an inner ring; and retaining said bag in place by a first set of spikes of different lengths that project radially inwardly from the collar to engage the handle directly, and by a second set of spikes that project radially inwardly from the collar to urge said bag against said handle.

* * * * *